United States Patent [19]

Komoschinski et al.

[11] Patent Number: 6,008,420

[45] Date of Patent: Dec. 28, 1999

[54] PROCESS FOR THE PRODUCTION OF HALOGEN METHYL CYCLOPROPANES AND HIGHLY PURE HALOGEN METHYL CYCLOPROPANES

[75] Inventors: Joachim Komoschinski, Köln; Reinhold Gehring, Wuppertal, both of Germany

[73] Assignee: Bayer Aktiengesellschaft, Leverkusen, Germany

[21] Appl. No.: 09/137,387

[22] Filed: Aug. 20, 1998

[30] Foreign Application Priority Data

Feb. 23, 1996 [DE] Germany .......................... 196 06 761

[51] Int. Cl.$^6$ .................................................. C07C 17/16
[52] U.S. Cl. .............................................................. 570/253
[58] Field of Search ....................................... 570/253, 252

[56] References Cited

U.S. PATENT DOCUMENTS

| | | | |
|---|---|---|---|
| 3,433,791 | 3/1969 | Bentley | 260/285 |
| 3,474,101 | 10/1969 | Bentley | 260/285 |
| 4,739,057 | 4/1988 | Leone-Bay et al. | |
| 5,288,932 | 2/1994 | Kaufhold | |

FOREIGN PATENT DOCUMENTS

| | | |
|---|---|---|
| 0102833 | 8/1986 | European Pat. Off. . |
| 0251246 A1 | 1/1988 | European Pat. Off. . |
| 0565826 A1 | 10/1993 | European Pat. Off. . |

OTHER PUBLICATIONS

Beres, JA et al. "Synthesis and antibacterial activity of high alkyl barbituric acids" *Eur. J. Med. Chem.—Chimical Therapeutica,* (Nov./Dec. 1980), vol. 15, No. 6, pp. 571–573, published in Europe.

Hrubiec, RT and MB Smith. "Regioselective Route to Sterically Hindered Cyclopropylcarbinyl Halides" *J. Org. Chem.* (1984), vol. 49, No. 3, pp. 431–435 published in US.

*Primary Examiner*—Joseph K. McKane
*Attorney, Agent, or Firm*—Brinks Hofer Gilson & Lione

[57] ABSTRACT

The invention relates to a process for the preparation of halogenomethylcyclopropanes.

10 Claims, No Drawings

PROCESS FOR THE PRODUCTION OF HALOGEN METHYL CYCLOPROPANES AND HIGHLY PURE HALOGEN METHYL CYCLOPROPANES

BACKGROUND OF THE INVENTION

Halogenomethylcyclopropanes are important intermediates for the preparation of pharmaceuticals (see, for example, British Patent Specification 1 136 214, U.S. Pat. No. 3,433,791 and EP-OS (European Published Specification) 102 833). As is usual in the preparation of pharmaceuticals, the purity for the intermediates required for this purpose should be as high as possible.

It is known to prepare halogenomethylcyclopropanes by reacting the corresponding alcohols with phosphorus trihalides. In accordance with Eur. J. Med. Chem.-Chim. Therap. 15, 571 (1980), however, a reaction temperature of −10° C. leads to over 70% undesired halogenocyclobutane. Even at temperatures of −65 and −80° C., which are difficult to control from a technical point of view, the undesired halogenocyclobutane still amounts to 8.0 and 4.3%, respectively.

In accordance with a different process, halogenomethylcyclopropanes are prepared by reacting the corresponding alcohols with methanesulphonyl halides in the presence of trialkylamines. This process, however, requires complicated dosing and temperature control (see EP-OS (European Published Specification) 565 826), if moderately pure products are to be obtained. To do this on an industrial scale requires complex measuring and control techniques and the reaction needs to be carried out extremely carefully.

Halogenoalkyls can also be prepared from hydroxyalkyls by reacting these with arylphosphorus halides (see EP-OS (European Published Specification) 251 246), for which purpose triarylphosphorus dihalides are generally employed, from which arylphosphorus tetrahalides are prepared in situ with elemental halogen. This process has not been applied to the conversion of hydroxymethylcyclopropanes into halogenomethylcyclcopropanes. Moreover, triarylphosphorus dihalides are not readily accessible.

In the process which has been the most advantageous to date, hydroxymethyl cyclopropane is added to a mixture of hexachloroacetone and triphenylphosphine, obtaining apparently pure chloromethylcyclopropane in yields of 80 to 90% (see J. Org. Chem. 49, 431 (1984)). The same reference describes the preparation of bromomethylcyclopropane by treating a mixture of hydroxymethylcyclopropane, triphenylphosphine and dimethylformamide with elemental bromine. At a reaction temperature of −10° C., the product is said to be free from linear alkyl bromides and bromocyclobutane and can be obtained in a yield of 72%. However, even at room temperature, linear bromobutene is indicated as the main product. Reproduction at −10° C. has revealed that the bromomethylcyclopropane obtained contains 0.6% by weight of linear impurities (see the present Comparison Example 1). In accordance with the reference, a very small excess of bromine is employed (98.9 mmol of bromine per 97.1 mmol of hydroxymethylcyclopropane).

The disadvantages of this process are the purity of the halogenomethylcyclopropane obtained, which is still unsatisfactory, the accessibility and manageability of hexachloroacetate, which are a problem, and the fact that the preparation processes for chloro- and bromomethylcyclopropanes differ. A particular problem is the contamination of the halogenomethylcyclopropanes obtained with linear compounds, in particular 1-halogeno-3-butenes, since the physical properties of linear halogenobutenes are virtually no different to those of the corresponding halogenomethylcyclopropanes. This is why the undesired linear compounds cannot be separated from the desired halogenomethylcyclopropanes by customary methods, for example by distillation.

DESCRIPTION OF THE INVENTION

There has now been found an improved process for the preparation of halogenomethylcyclopropanes of the formula

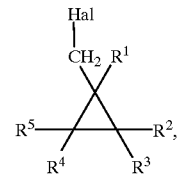

(I)

in which
Hal represents chlorine or bromine and
$R^1$ to $R^5$ independently of one another represent in each case hydrogen, optionally substituted $C_1$–$C_{10}$-alkyl or optionally substituted $C_6$–$C_{10}$-aryl
in which the corresponding hydroxymethylcyclopropanes of the formula

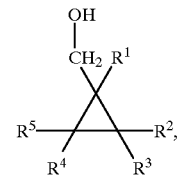

(II)

in which
$R^1$ to $R^5$ have the meaning given for formula (I)
are reacted with chlorine or bromine and an organic phosphorus compound and which is characterized in that chlorine or bromine is employed in an excess of at least 5 mol % (based on the hydroxymethylcyclopropane employed) and that the organic phosphorus compound employed is one of the formula (III)

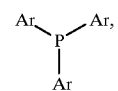

(III)

in which
Ar independently of one another represent in each case optionally substituted $C_6$–$C_{10}$-aryl.

If the radicals $R^1$ to $R^5$ are substituted $C_1$–$C_{10}$-alkyl, suitable substituents are, for example, halogen, in particular fluorine, chlorine and bromine, and cyano. 1 to 3 identical or different substituents may be present per alkyl group, for example. The alkyl groups may be straight-chain or branched.

If the radicals $R^1$ to $R^5$ are substituted $C_6$–$C_{10}$-aryl, suitable substituents are, for example, straight-chain and branched $C_1$–$C_6$-alkyl groups, corresponding alkoxy groups, corresponding halogenoalkyl groups, halogens and sulpho groups. Halogens, also halogens in halogenoalkyl groups, are preferably fluorine, chlorine and/or bromine. Halogenoalkyl groups may contain, for example, 1 to 3 identical or different halogen atoms. There may be, for example, 1 to 5 identical or different substituents per aryl group.

$R^1$ to $R^5$ independently of one another preferably represent hydrogen, $C_1$–$C_4$-alkyl which is optionally substituted by 1 to 3 substituents from the group consisting of fluorine, chlorine, bromine and cyano, and/or represent phenyl which is optionally substituted by 1 to 3 substituents from the group consisting of methyl, ethyl, methoxy, ethoxy, chloromethyl, dichloromethyl, trichloromethyl, chloroethyl, dichloroethyl, trichloroethyl, chlorine, bromine and sulphonyl.

Amongst the radicals $R^1$ to $R^5$, $R^1$, $R^3$ and $R^5$ especially preferably represent hydrogen and $R^2$ and $R^4$ independently of one another represent hydrogen, methyl, ethyl, n-propyl, i-propyl or phenyl. $R^1$ to $R^5$ very especially preferably represent hydrogen.

The radicals Ar can optionally be substituted in the same manner as given above for $R^1$ to $R^5$ with the meaning $C_6$–$C_{10}$-aryl. The Ar radicals are especially preferably identical and especially preferably represent phenyl, chlorophenyl, tolyl or methoxyphenyl. The radicals Ar very especially preferably represent phenyl.

The hydroxymethylpropanes of the formula (II) to be employed in the process according to the invention are known compounds and can be prepared in analogy to known compounds.

It is an essential feature of the present invention to employ chlorine or bromine in an excess of at least 5 mol % (based on hydroxymethylcyclopropane employed). For example, this excess may be 5 to 100 mol %. Preferred are excesses of 8 to 70 mol %, in particular those of 10 to 50 mol %. By using such excesses, this surprisingly results in halogenomethylcyclopropanes of the formula (I) which are distinguished by an especially low content of undesired secondary products. When following the procedure in accordance with the invention, it is in particular the content of linear 1-halogeno-3-butenes, which are difficult to remove, which amounts generally to less than 0.4% by weight and which can be reduced to less than 0.1% by weight, if desired even to less than 0.01% by weight.

The organic phosphorus compound employed can be an individual compound which comes under the formula (III), or else a mixture comprising a plurality of individual compounds which come under the formula (III).

Based on the alcohol of the formula (II) to be reacted, organic phosphorus compounds of the formula (III) can be employed for example, in equimolar amounts or in excesses of up to, for example, 1.5 times the equimolar amount. The phosphorus compound is preferably employed in an excess of 3 to 20 mol %, in particular 5 to 15 mol %, based on the alcohol.

The process according to the invention is preferably carried out in the presence of a solvent. Suitable solvents are, in particular, polar organic solvents, for example acetonitrile, dimethylformamide, dimethylacetamide and N-methylpyrrolidone. Dimethylformamide is preferred.

The process according to the invention can be carried out, for example, at temperatures in the range of −25 to +30° C. Preferred are −20 to +25° C., in particular −15 to +5° C.

The reaction mixture which is present after carrying out the process according to the invention can be worked up by processes known per se, for example by distillation. The process according to the invention allows halogenocyclopropanes of the formula (I) to be obtained in purities of over 95%, frequently even over 97% and in yields of over 70%, frequently over 75%. In particular, the content of interfering linear 1-halogeno-3-butenes which are difficult to remove is much lower than in the case of known processes, as already mentioned above. This is especially surprising, since the prior art only suggested a favorable effect of extremely low reaction temperatures on a reduced formation of undesired secondary products; this, however, was certainly far short of the good results which can be obtained with the process according to the invention.

The triarylphosphine oxides obtained as secondary product can be converted back into the corresponding triarylphosphines in a simple manner by means of reduction and then employed again as compounds of the formula (III).

The present invention furthermore relates to halogenomethylcyclopropanes of the formula (I)

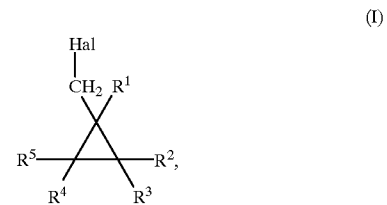

(I)

in which
Hal represents chlorine or bromine and
$R^1$ to $R^5$ independently of one another represent in each case hydrogen, optionally substituted $C_1$–$C_{10}$-alkyl or optionally substituted $C_6$–$C_{10}$-aryl
with a content of linear 1-halogeno-3-butenes of less than 0.4% by weight, in particular less than 0.1% by weight.

The present invention furthermore relates to bromomethylcyclopropane with a content of open-chain halogenoalkenes of less than 0.4% by weight, in particular less than 0.35% by weight, very especially 0.005 to 0.35% by weight.

EXAMPLES

Percentages are by weight, unless otherwise specified.

Example 1 (for comparison)

1250 ml of dimethylformamide were placed into the reaction vessel, and then 280.8 g of triphenylphosphine and then 70 g of hydroxymethylcyclopropane were added, the mixture was stirred for 30 minutes at room temperature under a nitrogen atmosphere, and the solution was subsequently cooled to −10° C. Then, 158.3 g of bromine (that is to say 2 mol % more than theoretically required) were metered in in the course of 4 hours. The reaction mixture was worked up by distillation. Bromomethylcyclopropane was obtained in a yield of 77.5% of theory. The purity of the product was over 97%, the open-chain halogenoalkanes amounted to 0.6%.

Example 2

The process was as in Example 1, but bromine was employed in an excess of 10 mol %. Yields and purities of the product were as specified in Example 1, but the open-chain halogenoalkenes amounted to only 0.35%.

Example 3

The process was as in Example 1, but bromine was employed in an excess of 25 mol %. Yields and purities of the product were as specified in Example 1, but the open-chain halogenoalkanes amounted to only 0.071%.

Example 4

The process was as in Example 1, but bromine was employed in an excess of 50 mol %. The product yields and purities achieved were as specified in Example 1, but the open-chain halogenoalkanes only amounted to 0.005%.

Example 5

The procedure was as in Example 2, but instead of bromine, a corresponding amount of chlorine was employed, and chloromethylcyclopropane was obtained in a corresponding yield and purity.

We claim:

1. A process for preparing a compound of the formula (I):

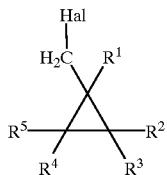

wherein Hal is chlorine or bromine, and $R^1$ to $R^5$ are, each independently, hydrogen, unsubstituted or substituted $C_1$–$C_{10}$-alkyl, or unsubstituted or substituted $C_6$–$C_{10}$-aryl, comprising reacting a compound of the formula (II)

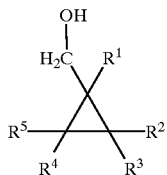

wherein $R^1$ to $R^5$ are the same as above
with chlorine or bromine, the chlorine or bromine being in an excess of at least 5 mol % compared to the compound of formula (II), and
with an organic phosphorus compound of the formula (III)

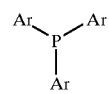

wherein each Ar is independently an unsubstituted or substituted $C_6$–$C_{10}$-aryl.

2. The process of claim 1 wherein the substituents for the $C_1$–$C_{10}$-alkyl of $R^1$ to $R^5$ are halogenyl or cyano.

3. The process of claim 1 wherein the substituents for the $C_6$–$C_{10}$-aryl of $R^1$ to $R^5$ are selected from the group consisting of straight-chain $C_1$–$C_6$-alkyl, straight-chain $C_1$–$C_6$-alkoxy, straight-chain $C_1$–$C_6$-halogenoalkyl, branched $C_1$–$C_6$-alkyl, branched $C_1$–$C_6$-alkoxy, branched $C_1$–$C_6$-halogenoalkyl, halogenyl and sulpho.

4. The process of claim 1 wherein the substituents for $C_6$–$C_{10}$-aryl of Ar are selected from the group consisting of straight-chain $C_1$–$C_6$-alkyl, straight-chain $C_1$–$C_6$-alkoxy, straight-chain $C_1$–$C_6$-halogenoalkyl, branched $C_1$–$C_6$-alkyl, branched $C_1$–$C_6$-alkoxy, branched $C_1$–$C_6$-halogenoalkyl, halogenyl and sulpho.

5. The process of claim 1 wherein $R^1$, $R^3$, and $R^5$ are hydrogen, and $R^2$ and $R^4$, are, each independently, hydrogen, methyl, ethyl, n-propyl, i-propyl, or phenyl, and Ar is phenyl, chlorophenyl, tolyl, or methoxyphenyl.

6. The process of claim 1 wherein $R^1$ and $R^5$ are hydrogen, and each Ar is phenyl.

7. The process of claim 1 wherein an excess of 8–70 mol % of chlorine or bromine is used.

8. The process of claim 1 wherein the reacting is carried out in a polar organic solvent.

9. The process of claim 8 wherein the polar organic solvent is selected from the group consisting of acetonitrile, dimethylformamide, dimethylacetamide, and N-methylpyrrolidone.

10. The process of claim 1 wherein the reacting is carried out at a temperature range from −25 to 30° C.

* * * * *

UNITED STATES PATENT AND TRADEMARK OFFICE
CERTIFICATE OF CORRECTION

PATENT NO. : 6,008,420
DATED : December 28, 1999
INVENTOR(S) : Joachim Komoschinski et al.

Page 1 of 1

It is certified that error appears in the above-identified patent and that said Letters Patent is hereby corrected as shown below:

<u>Title page,</u>
Line 1, under "Foreign Application Priority Data", insert the following:

-- Feb. 10, 1997     [PCT/EP]     97/00607 --.

Signed and Sealed this

Twenty-fifth Day of December, 2001

Attest:

JAMES E. ROGAN
*Attesting Officer*     *Director of the United States Patent and Trademark Office*